United States Patent [19]

Zipes

[11] 4,384,585
[45] May 24, 1983

[54] SYNCHRONOUS INTRACARDIAC CARDIOVERTER

[75] Inventor: Douglas P. Zipes, Indianapolis, Ind.

[73] Assignee: Medtronic, Inc., Minneapolis, Minn.

[21] Appl. No.: 241,314

[22] Filed: Mar. 6, 1981

[51] Int. Cl.³ ............................................. A61N 1/36
[52] U.S. Cl. .......................... 128/419 D; 128/419 PG
[58] Field of Search ............ 128/419 D, 419 PG, 705, 128/703

[56] References Cited

U.S. PATENT DOCUMENTS 3,527,228 9/1970 McLaughlin .................. 128/419 D
3,759,248 9/1973 Valiquette ........................... 128/703
3,857,398 12/1974 Rubin ............................. 128/419 D Primary Examiner—William E. Kamm
Attorney, Agent, or Firm—Robert C. Beck; John L. Rooney; Joseph F. Breimayer

[57] ABSTRACT

An implantable medical device to deliver cardioverting energy to cardiac tissue in synchrony with detected ventricular depolarizations. The energy renders refractory, areas of the heart associated with a reciprocating or automatic tachycardia, thus reverting these tachyarrhythmias to normal sinus rhythm without the risk of stimulating the heart during the vulnerable portion of repolarization.

2 Claims, 2 Drawing Figures

SYNCHRONOUS INTRACARDIAC CARDIOVERTER

BACKGROUND OF THE INVENTION

1. Field of the Invention

This invention relates to an implantable medical device that delivers sufficient electrical energy to cardiac tissues to terminate (cardiovert) tachycardias and thus restore normal sinus rhythm.

2. Description of the Prior Art

Implantable material devices for the therapeutic stimulation of the heart are well known in the art from U.S. Pat. No. 3,478,746 issued to Wilson Greatbatch, which discloses a demand pacemaker. The demand pacemaker delivers electrical energy (5–25 microjoules) to the heart to initiate the depolarization of cardiac tissue. This stimulating regime is used to treat heart block by providing electrical stimulation in the absence of naturally occurring spontaneous cardiac depolarizations.

Another form of implantable medical device for the therapeutic stimulation of the heart is the automatic implantable defibrillator (AID) described in U.S. Pat. Nos. 3,614,954 and 3,614,955 to Mirowski, et al. These AID devices deliver energy (40 joules) to the heart to interrupt ventricular fibrillation of the heart. In operation, the AID device detects the ventricular fibrillation and delivers a nonsynchronous high-voltage pulse to the heart through widely spaced electrodes located outside of the heart, thus mimicking transthoracic defibrillation. This prior art technique requires both a limited thoracotomy to implant an electrode near the apical tip of the heart and a pervenous electrode system located in the superior vena cava of the heart. In practice, these devices have received limited usage due to the complexity of their implantation, their relatively large size and short operating life, and to the small numbers of patients who might benefit from it.

Another example of a prior art implantable cardioverter includes the device taught by U.S. Pat. application Ser. No. 58,847 to Engle, et al. This device detects the onset of tachyarrhythmia and includes means to monitor or detect the progression of the tachyarrhythmia so that progressively greater energy levels may be applied to the heart to interrupt the arrhythmia.

A last example is that of an external synchronized cardioverter, described in *Clinical Application of Cardioversion* in Cardiovascular Clinics, 1970,2, pp. 239-260 by Douglas P. Zipes. This external device described is synchronized with ventricular depolarization to ensure that the cardioverting energy is not delivered during the vulnerable T-wave portion of the cardiac cycle.

SUMMARY OF THE INVENTION

In contrast to the prior art, the implantable synchronous intracardiac cardioverter of the present invention includes circuitry to detect the intrinsic depolarizations of cardiac tissue and includes pulse generator circuitry to deliver moderate energy level stimuli (in the range of 0.1–10 joule) to the heart in synchrony with the detected cardiac activity. The functional objective of this stimulating regime is to depolarize areas of the myocardium involved in the genesis and maintenance of reentrant or automatic tachyarrhythmias at lower energy levels and with greater safety than is possible with nonsynchronous cardioversion. Nonsynchronous cardioversion always incurs the risk of precipitating ventricular fibrillation and sudden death. Synchronous cardioversion delivers the shock at a time when the bulk of cardiac tissue is already depolarized and is in a refractory state.

It is expected that the safety inherent in the use of lower energy levels, the reduced trauma to the myocardium, and the smaller size of the implanted device will expand the indications for use for this device beyond the patient base of prior art automatic implantable defibrillators. Since many episodes of ventricular fibrillation are preceded by ventricular (and in some cases, supraventricular) tachycardias, prompt termination of the tachycardia may prevent ventricular fibrillation.

Additional circuitry may be included to provide a demand-pacing function in addition to the previous described cardioverting output. It is also anticipated that the amount of energy delivered can be controlled (programmed) by an external unit to reduce the joules delivered or increase the amount to a value that will be capable of terminating ventricular fibrillation. Finally, the device may be programmed to deliver the energy automatically after sensing particular parameters of a tachycardia or it can be programmed to deliver the energy only when an external magnet is held in place over the pulse generator.

DETAILED DESCRIPTION OF THE PREFERRED EMBODIMENT

Figure 1:
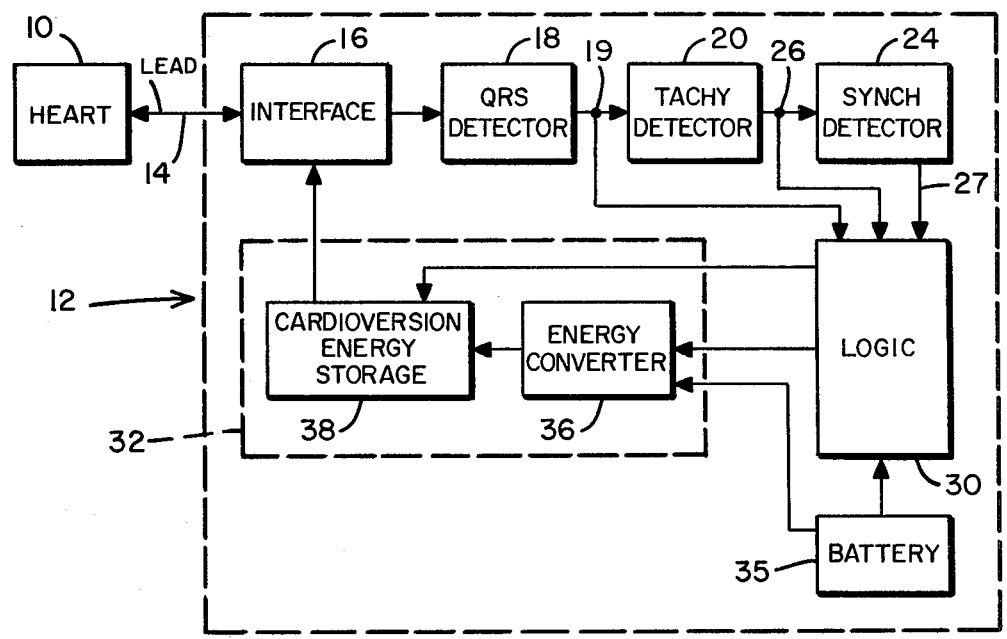
FIG. 1 is a block diagram showing the functional organization of the synchronous intracardiac cardioverter.

An understanding of the operational mode of the present invention is facilitated by a brief discussion of the physiology of the heart and the theoretical mechanisms of reentrant tachycardias.

The normal pumping action of the heart results from highly organized electrical activity in the cardiac tissue. Each natural spontaneous heart beat begins with an electrical discharge from the sino-atrial node (S-A) located in the right atrium of the heart. This electrical impulse is conducted through tissues which result in the progressive depolarization of the atrial tissue causing it to contract. The contraction forces blood from the atrium through the heart valves into the ventricles. The electrical impulse from the atrium is communicated to the ventricles through the atrio-ventricular node (A-V), which is located on the septal wall dividing the right and left heart. The electrical signal is delayed in this conductive node for approximately 0.15 seconds and is then transmitted through the His bundle and its branches to the Purkinje fibers which discharge ventricular muscle, causing the ventricles to contract in an organized fashion and pump blood throughout the body. In the healthy heart, this normal sinus rhythm may be repeated between 60 and 120 times per minute. In the diseased heart, however, a number of arrhythmias may occur which disrupt this normal activity. The type of arrhythmias are divided into two groups: tachyarrhythmias, which are generally characterized by heart rates faster than normal, and bradarrhythmias, which are characterized by heart rates lower than normal.

The characterization and origin of a tachyarrhythmia is of practical significance since the success of drug treatment of such disorders depends to a great degree on the accurate determination of their origin and cause. In contrast, when cardioversion is selected to treat these disorders, the characterization and origin of the arrhythmia is of less significance. For example, it has been shown that transthoracic DC electrical shock can successfully terminate many different types of tachyarrhythmias. See, for example, *Cardioversion*, B. Lown, Med. Ann. D.C., 38:543, 1969.

Tachyarrhythmias may be characterized further by their location of origin. For example, the origin of supraventricular tachyarrhythmias is in the atria; and its maintenance involves the atria and sometimes ventricles. Ventricular tachyarrythmias originate and are maintained within the ventricles and sometimes conduct to the atria. A separate group of tachyarrhythmias are called flutter or fibrillation. Flutter is generally characterized by rapid, organized heart activity and, when involving the ventricles, low cardiac output. Fibrillation is characterized by highly disorganized electrical activity that results in virtually no cardiac output when it involves the ventricles. In some patients there may be a progression from an organized tachycardia to fibrillation which will lead to death if the site of the fibrillation is the ventricles. In many patients, ventricular tachycardia precedes the onset of ventricular fibrillation; and if the former can be terminated, generally with small amounts of energies, the latter can be prevented. Some patients exhibit chronic atrial flutter or fibrillation which may be debilitating but does not cause death, and other patients exhibit occasional or paroxysmal attacks of ventricular tachycardias which require cardioversion. See, for example, "Cardiac Arrhythmias," in *Current Diagnosis*, W. B. Saunders Co., 1977, pp. 377–396, by Douglas P. Zipes, M.D.

With an appropriate lead system, the present invention may be used to treat both supraventricular and ventricular tachyarrhythmias that are either chronic or intermittent. The treatment regime embodied in the present invention calls for synchronous cardioversion of the arrhythmia. Cardioversion, as used herein, refers to the use of electrical stimulation to terminate an arrhythmia or revert the heart to normal sinus rhythm; and the term cardioversion, as used herein, may refer to the treatment of any kind of supraventricular or ventricular tachyarrhythmia also including fibrillation or flutter. The use of electrical energy to terminate ventricular fibrillation transthoracically has been known since the 1930s and has been successfully employed in a clinical setting since the early 1960s. For example, see *Electrical Reversion of Cardiac Arrhythmias*, by Bernard Lown, Brit. Heart J., 1967, 29, 469. Electrical energy has also been used to terminate tachycardias transthoraciacially. Intracardiac defibrillation has been performed successfully by Mirowski, et. al.; but no one has performed, or developed a commercial device to perform, synchronized intracardiac cardioversion, which is the nature of the present device.

The functional objective of the apparatus of the invention is to deliver sufficient energy to the heart in synchrony with a detected cardiac depolarization to depolarize the parts of the heart such as reentrant pathways which sustain the tachyarrhythmia and thus cause the tachyarrhythmia to terminate. Synchrony with the R-wave is important since a shock delivered at such a time does not result in a manifest ventricular response, nor does it interrupt the normal repolarization potential of the myocardium characterized by the T-wave. This stimulation regime permits the termination of the tachyarrhythmia at a lower energy level and with greater safety than is possible with prior art devices.

Turning now to FIG. 1, the patient's heart 10 is coupled to the synchronous intracardiac cardioverter 12 through an appropriate lead 14 and lead interface 16. It is expected that a specialized endocardial lead system with relatively large area electrodes will be suitable for transvenous synchronized cardioversion. The lead interface 16 includes circuitry to isolate the QRS detector 18 from the high voltage present during the delivery of a cardioverting pulse.

Depolarization signals from the heart are communicated to the sensing amplifier or QRS detector 18 where they are detected. Such sense amplifiers are known in the art from U.S. Pat. application Ser. No. 957,825, filed Nov. 6, 1978, which is incorporated herein by reference. A subsequent tachyarrhythmia detector section 20 is coupled to the QRS detector through connection 19 to detect tachyarrhythmia based upon the electrogram information producing a tachy detect signal.

The synchrony detector 24 receives the tachy detect signal through connection 26. The output 27 of the synchrony detector is communicated to an appropriate logic section 30 which controls the pulse-forming circuitry and triggers the delivery of the cardioverting pulse in response to the detected tachyarrhythmia. The synchrony detector 24 insures that the cardioverting pulse is delivered to the cardiac tissue concurrent with a detected ventricular depolarization of cardiac tissue. The pulse generator portion of the circuitry 32 receives power from a battery 35 and a DC/DC energy converter 36 which supplies energy to the energy storage circuitry 38.

In operation, the electrogram information from the heart 10 is processed by the device which detects depolarizations of cardiac tissue and produces a sense signal indicative of this fact. This sense amplifier output is processed by a tachyarrhythmia detector to determine the presence or absence of a tachyarrhythmia. The tachyarrhythmia detection circuitry may operate in any known manner, and more specifically, may determine the time interval between successive cardiac depolarizations and produce a tachy detect signal if either the average detected heart rate is above a preset threshold for a limited time period and/or if the detected heart rate accelerates by a preset amount. An alternative detection criteria may include memory means for recording a succession of R to R intervals and means for detecting the departure of selected beats from this historic data base. A final detection criteria within the scope of this invention includes a waveform analysis of the electrogram information involving pattern recognition of time domain or frequency domain characteristics of the tachyarrhythmia signal.

If a tachyarrhythmia is detected, the logic section 30 will initiate a discharge of the energy storage section 38 to produce a cardioverting output. The synchrony detector will insure that the energy is delivered to the heart 10 concurrent with a detected ventricular depolarization. The synchrony detection circuitry may comprise combinatorial logic to activate the cardioverting pulse generator circuitry 32 only when a tachy detect signal has been produced by the tachyarrhythmia detection circuitry. After the delivery of the cardioverting energy, the device will monitor the heart activity to determine if the arrhythmia has been terminated. If the arrhythmia is continuing, then additional cardioverting pulses will be delivered to the heart. These may be of the same or greater energy.

Additionally, a demand pacemaker function may be added to the device. This may be desirable for pacing the heart after the cardioverting energy has been delivered to the heart since the normal sinus rhythm may be momentarily suppressed with termination of the tachyarrhythmia.

Figure 2:
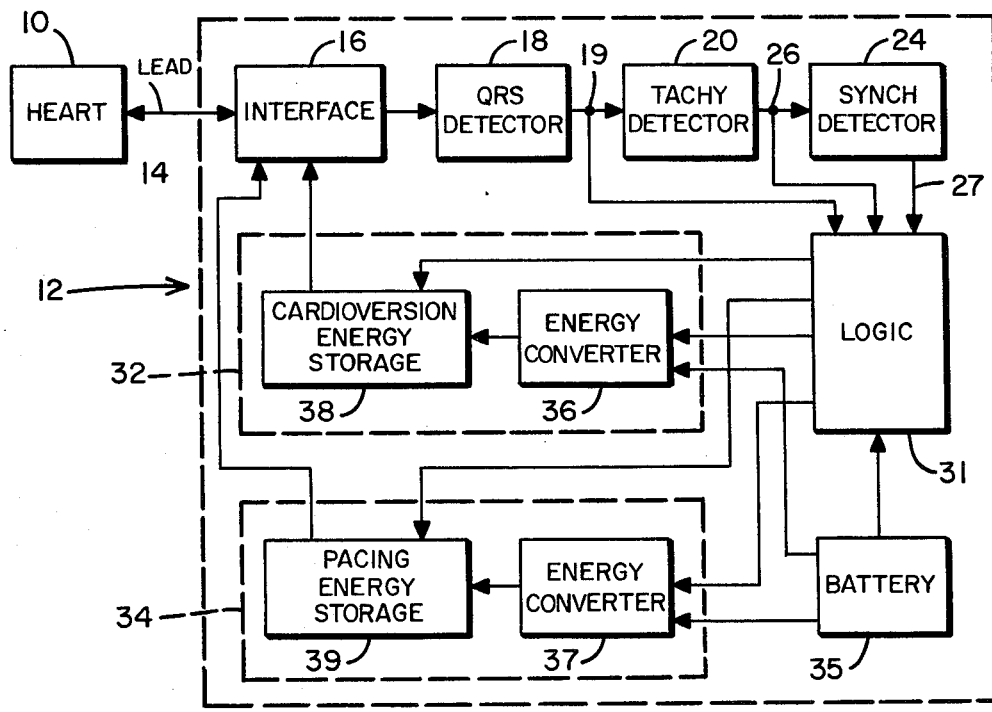
FIG. 2 is a block diagram showing the synchronous intracardiac cardioverter, integrated with a demand pacemaker.

Turning to FIG. 2, the synchronous intracardiac cardioverter is shown combined with demand pacing circuitry. In this figure, like components are numbered as in FIG. 1. The principal addition is a lower energy pacing pulse generator 34 coupled to the lead interface. This pulse generator comprises an energy converter 37 for charging the pacing energy storage circuitry 39 from the battery 35. In operation, logic 31 receives the signal from the QRS detector 18 and resets an escape interval timing system. If no cardiac depolarization is detected within the escape interval, a pacing pulse will be delivered to the heart. The integrated demand pacer with the synchronous cardioverter permits the device to initiate a cardiac depolarization if a previously delivered cardioverting pulse has prevented the rapid establishment of a normal sinus rhythm.

It is apparent from the foregoing description that various modifications may be made to the present invention without departing from the scope of the invention.

I claim:

1. An implantable medical device for the electrical termination of tachyarrhythmia comprising:

sensing means responsive to cardiac depolarizations for producing a sense signal indicative of naturally occurring cardiac activity;

detection means responsive to said sensing means for detecting cardiac tachyarrhythmia for producing a tachyarrhythmia signal indicative of such tachyarrhythmia;

pulse generator means responsive to a stimulus signal for delivering a cardioverting pulse to cardiac tissue in response to said stimulus signal;

stimulus signal generating means responsive to said detection means for generating an output stimulus signal concurrent with each detected depolarization; and means for ensuring that the cardioverting pulse is delivered to cardiac tissue concurrent with a detected ventricular depolarization of the cardiac tissue.

2. The device of claim 1 further including:

a pulse generator responsive to said sensing means for producing a cardiac-stimulating pacing pulse if no cardiac depolarization is detected within a preset escape interval.

* * * * *